United States Patent

Kath et al.

Patent Number: 5,516,491
Date of Patent: May 14, 1996

[54] DISPOSABLE REACTOR VESSEL

[75] Inventors: Gary S. Kath, Scotch Plains; Gregory W. King, Carteret; Kevin Chapman, Scotch Plains, all of N.J.

[73] Assignee: Merck & Co., Inc., Rahway, N.J.

[21] Appl. No.: 281,813

[22] Filed: Jul. 28, 1994

[51] Int. Cl.⁶ ............................................. B01L 3/00
[52] U.S. Cl. ...................... 422/102; 422/211; 422/239; 435/283.1; 435/309.1; 935/88
[58] Field of Search ....................... 422/102, 211, 422/239, 58, 65, 61; 435/296, 299; 935/88; 436/178; 222/211, 204, 416, 189.1, 189.11, 189.06

[56] References Cited

U.S. PATENT DOCUMENTS

| | | | |
|---|---|---|---|
| 675,042 | 5/1901 | Hepburn | 422/102 |
| 730,674 | 6/1903 | Lyons | 422/102 |
| 785,524 | 3/1905 | Shea | 422/102 |
| 1,498,443 | 6/1924 | Fulsher | 422/102 |
| 2,476,093 | 7/1949 | Hirsch | 422/102 |
| 3,259,462 | 7/1966 | Anscherlik | 222/204 |
| 3,705,018 | 12/1972 | Taylor | 422/102 |
| 3,977,598 | 8/1976 | McDonald | 422/72 |
| 3,983,037 | 9/1976 | Lee et al. | 422/72 |
| 4,367,198 | 1/1983 | Scordato et al. | 422/102 |
| 4,567,021 | 1/1986 | Sakagami | 422/102 |

OTHER PUBLICATIONS

Webster's Ninth New Collegiate Dictionary, Merriam Webster 1990, p. 705.

Primary Examiner—Jill Warden
Assistant Examiner—Jan M. Ludlow
Attorney, Agent, or Firm—Francis P. Bigley; Mark R. Daniel

[57] ABSTRACT

A disposable transportable reactor vessel can be prepared by modifying an eye-dropper pipette. A HDPE plug is inserted in one end of the pipette to permit selective passage of fluid while preventing resin flow. The pipette is looped into the shape of a u-tube and inserted into a holder such that the pipette is axially aligned with the holder to facilitate use in a robotic system.

6 Claims, 2 Drawing Sheets

DISPOSABLE REACTOR VESSEL

BACKGROUND OF THE INVENTION

Solid phase chemical reactions conducted in small scale reactor vessels are conducive to automation; at least one chemical synthesizer is commercially available. This provides a reactor block with 48–96 reaction vessels, each of which can be different. Many steps still require a manual operation or are difficult to automate. For instance, the following operations present problems or are awkward:

loading the resins;

loading the reagents;

installing the septum;

separating blocks and installing cleavage rack;

separating block, removing vials and loading drier;

re-packaging samples in containers suitable for specific programs;

cleaning reactor block; and finally, reactor block is bulky and heavy making it difficult to transport.

These are also disadvantages in using the reactor block:

solvents occasionally get under septum sheet and can potentially get into an adjacent well;

Teflon u-tube seal at bottom of reactor leaks;

u-tube-to-exit tube transition has areas where fluid entrapment may occur;

frits, septum and block may need to be replaced after a number of runs;

HDPE reactor block may get stained and contaminated when using certain chemistries, and drops inadvertently falling from robot tip can collect on the flat top of reactor septum.

Another approach is to have a system which operates in a serial mode where a single reactor or a group of reactors is handled individually. The system would consist of modular stations which would perform specific tasks and operate independently of the transport robot. The system would be scheduled to stagger the starting point of the reactors in a manner which would make the best use of the robot time (i.e., while one group of reactors are being mixed another group of reactors are being cleaved). Since multiple operations can occur simultaneously and independently, throughput can be increased and it would be possible to run reactors with different chemistries, mixing times and recipes.

One could envision developing a chemical synthesizer which is totally automated where a scientist would sit down at a computer and develop a recipe to synthesize a compound using a large selection of reagents and resins. The software would then send the appropriate commands to the automated synthesizer. The synthesizer would incorporate a robot system which would select a clean reactor vessel, add resins, add reagents, mix, drain, . . ., cleave sample, label container, dry sample, analyze sample and packaged sample for shipment.

This system would necessitate a reaction vessel suitable for automation. Ideally, the vessel would be inert, sealed, easily transported by a robot system, permit thorough resin washing and mixing, be light weight, disposable, and low cost.

SUMMARY OF THE INVENTION

An object of the present invention is to provide a reactor vessel which possess all of these properties. Such a reactor vessel can be provided by modifying a commercially available blow-molded eye-dropper pipette. Other objects of the invention will be evident from the following description of a preferred embodiment with reference to the accompanying drawings.

BRIEF DESCRIPTION OF THE DRAWINGS

FIG. 2 represents the placement of the porous plug in the neck of the pipette;

FIG. 3 represents the binding, or looping the stem of the pipette into the shape of a u-tube to form the shaped reaction vessel.

FIG. 5 illustrate an air jet mixer system;

FIG. 6 an electro-magnet vibrator mixer system.

DESCRIPTION OF THE PREFERRED EMBODIMENT

Figure 1:
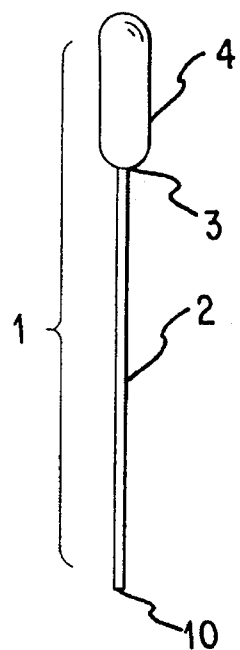
FIG. 1 is a schematic view of a commercially available blow-molded eye-dropper pipette.
Figure 2:
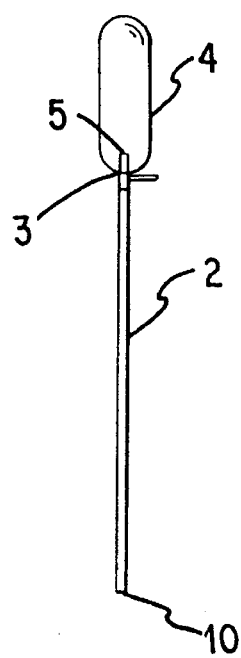
FIGS. 2 and 3 illustrate the manufacturing process of the reaction vessel of this invention.
Figure 3:
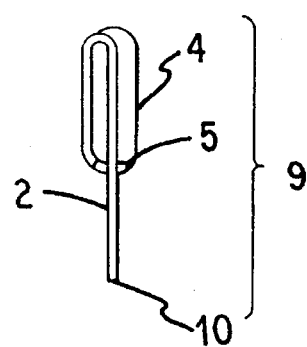

The reactor vessel apparatus illustrated in the drawings comprises a blow-molded modified eye-dropper pipette. The unmodified eye-dropper pipette, or vessel, shown generally at 1 in FIG. 1 is comprised of a squeezer 4 and a stem 2 having tip 10; the vessel and stem are joined at the neck 3. To modify and manufacture the inventive device, first, a high density polyethylene (HDPE) plug is inserted into the stem 2, up to the neck 3 of the vessel's squeezer 4. The porous plug serves to pass fluid but not resin. Referring to FIG. 3, the stem 2 of the pipette vessel 4 is then looped into the shape of a u-tube around the vessel 4 until the tip 10 points downward, forming a smooth curved shape 9 of the single-piece construction. Other materials can be used for the porous plug, as long as they are inert to the reaction, yet capable of serving as the filter when the solid state reaction is terminated and drained. Suitable porous plugs can be made of glass, sintered metal, nylon, polysulfone, polycarbonate, polyethafluoroethylene (PTFE), and the like.

The eye-dropper pipette is commercially available from a number of sources, and is blow-molded of polypropylene. Its volume is about 5 cc, but it can be 2–20 cc. Polypropylene can hold up to many solvents used for solid phase chemistry, and the low cost of such vessels would permit the vessels to be discarded after use which would insure a clean contamination free vessel at the start of each reaction. It is of course possible to blow-mold vessels of other materials, such as teflon, polyethylene or glass if necessary.

Figure 4:
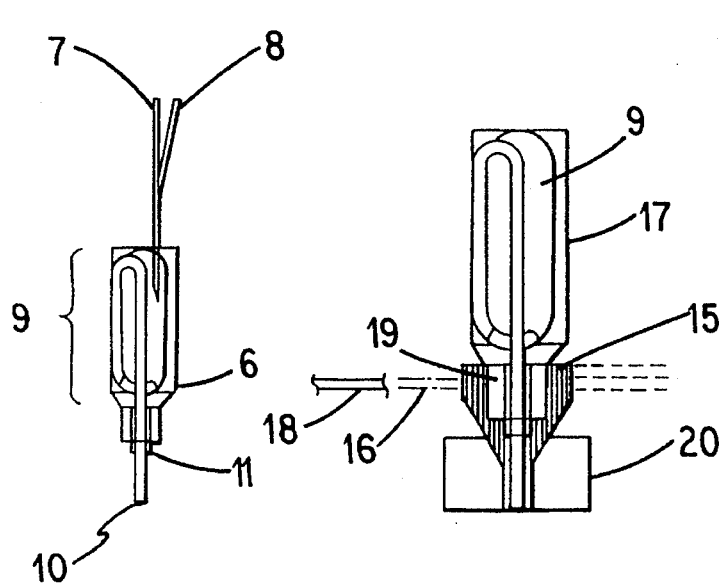
FIG. 4 is a schematic view of the reaction vessel in a holder, such as a syringe barrel.

To use the reaction vessel, see FIG. 4; the looped pipette 9 is slid into a light weight holder 6 in a manner that the tip 10 exits the center bottom 11 of the holder 6. A central exit point is advantageous when using robotics. The holder illustrated in FIG. 4 is a syringe barrel, but other functionally similar holders can also be used.

Since the vessel is molded of flexible plastic it can be easily pierced with a syringe needle. To fill the vessel with resin, a resin-solvent slurry would be dispensed into the top of the pipette's squeezer using a syringe needle 7. During dispensing, the vessel needs to be open to the atmosphere;

this is accomplished with either a coaxial needle or second hole/pierced in the top of the vessel. Upon piercing, the polypropylene partially reseals the hole, acting as a septum. Tests show with a small hole present them is slow evaporation of solvents when using a polypropylene vessel pierced by a 20 gauge syringe needle. It would also be possible to dip the vessel in silicon rubber to provide a better septum seal.

The vessel would be drained by pressurizing using a coaxial needle 8 supply air, nitrogen or helium. When pressurized, the liquid would flow through the u-tube to a drain. It would also be possible to pull a vacuum underneath the vessel.

The u-tube arrangement and HDPE frit permits solvents and resins to be retained in the vessel. Ideally, individual mixing of each vessel would be desired so other vessels could continue to mix while draining and dispensing operations occur on an individual vessel.

Figure 5:
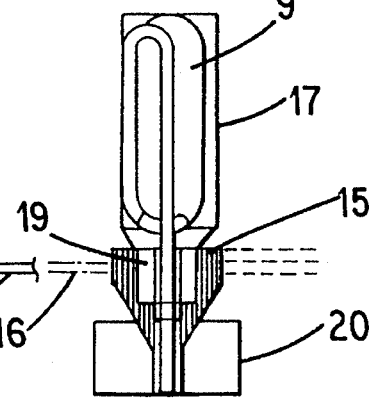
FIGS. 5 and 6 show the vessel in other holders fitted for different mixing methods.
Figure 6:
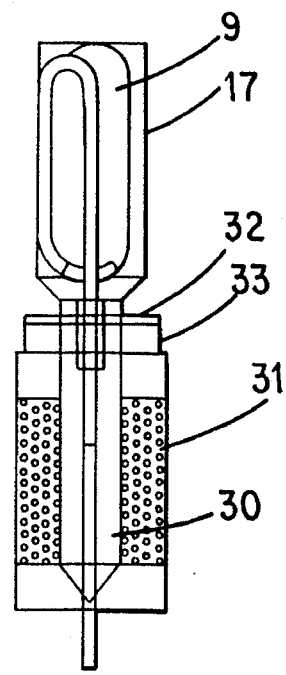

Two possible mixing methods of an individual transportable reactor are shown. FIGS. 5 and 6. In FIG. 5, a small rotor 15 is attached to the bottom 16 of the vessel holder 17 which would permit the vessel 9 to be air jet spun using an air feed tube 18 blowing an air jet 19 so that the rotor 15 revolves around bearing 20.

Another method is illustrated in FIG. 6, in which an iron slug 30 is attached to the bottom 16 of the vessel holder 17 which would permit electro-magnetic vibration mixing, using an electro-magnet 31 to vibrate the iron slug vertically against washer 32 and foam spring 33.

Both techniques illustrated in FIGS. 5 and 6 would permit vessels to be independently mixed and would permit the addition and draining of reagents without stopping the mixing of other reactor vessels. The mixing station would hold a number of reactor vessels and a drain tray would be positioned under the station.

If a transportable rack of reactor vessels is used, mixing is accomplished by vortexing or electro-magnetic vibrating the rack.

Once the reaction is complete, cleaving the sample from the resin is implemented by adding the cleavage solvent, mixing and positioning the vessel over the product container and pressurizing to empty the reactor vessel.

A hopper could feed the system with clean reactor vessels or rocks of vessels. To transport an individual vessel, the pipetter robot could pierce the vessel and move the reactor to the appropriate location (i.e., mixer rack, cleavage rack, disposal container). The septum action of a polypropylene reactor vessel will grip the needle and prevent the vessel from dislodging. To transport a vessel rack, a standard robot hand would be used.

Figure 7:
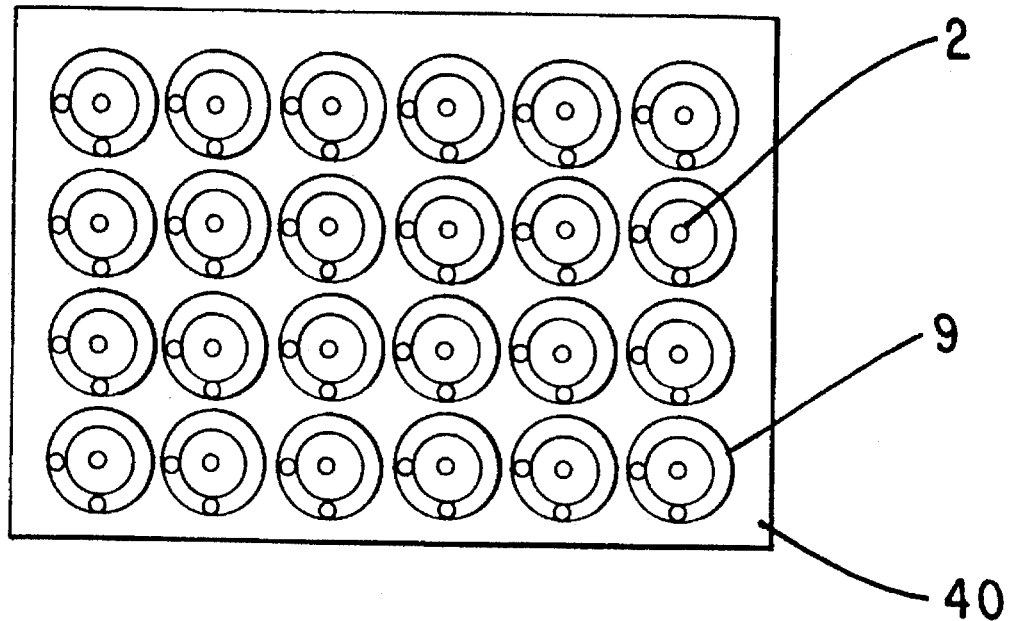
FIGS. 7 and 8 illustrate the top plain view, and a side schematic view, respectively, of a transportable rack of multiple reactor vessels.
Figure 8:
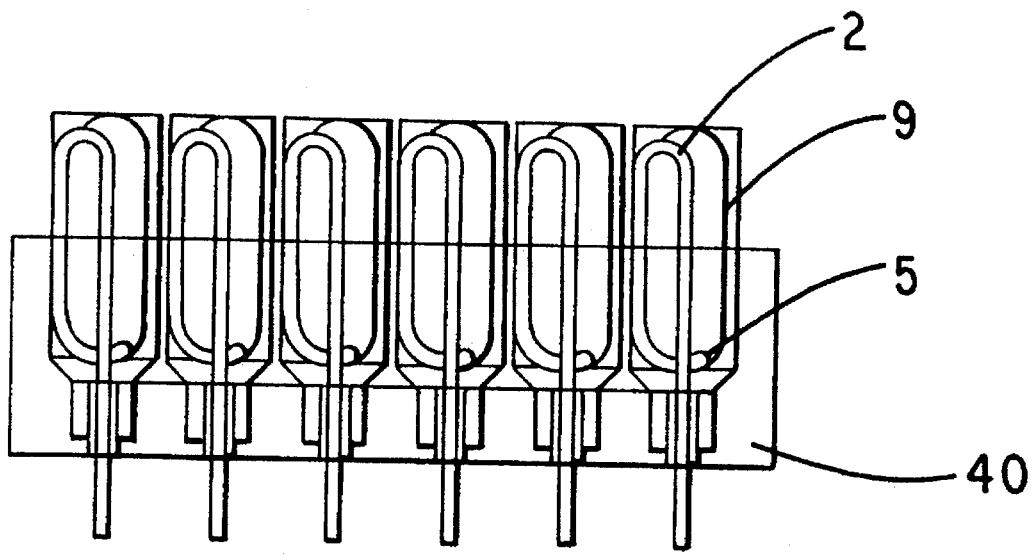

Although many uses can be envisioned for the reactor vessel of this invention, a serial solid phase synthesizer could be designed around a robot such as an HP ORCA. The robot would serve as a transport apparatus moving the reactors between independent workstations. Reactor vessels or racks containing a group of vessels would be loaded from a hopper. A rack of vessels is shown at FIGS. 7 and 8, with one rack 40 capable of holding 24 reactor vessels 9 each fitted with a HDPE plug 5 and with the stem 2 shaped into a u-tube. The assembly of the rack and vessels can also be called a reactor block. The rack 40 shown in FIGS. 7 and 8 is the same size as a micro-titer plate. The robot would transport the vessel to a free location in a resin filling station. The filling station would piece the reactor and dispense in the resin-slurry. Next the vessel would be moved to the mixing-draining-pipetting station. The pipetting station would dispense the various solvents. The vessel would be mixed for a time period and drained by piercing and pressurizing. Cleavage solvents would then be added, the vessel mixed and the vessel transported over the product vials. The product vials would be hopper fed and bar code labeled. The product in the reactor vessel would be drained by pressurizing. Once drained, the reactor vessel would be disposed.

The robot would then load the vials into a drier. When drying is complete, the vials containing the final product, would be positioned into a heat sealer. The heat sealer would melt and seal the neck of the vial and place the vial in a rack to be shipped to the chemist.

What is claimed is:

1. A reaction container for solid phase chemical synthesis utilizing solids, liquids and gases, the container comprising a one piece vessel and hollow stem combination, the vessel having a penetrable and at least partially resealable closed top end and a bottom end, the bottom end terminating in a hollow neck, the neck being integrally connected to the hollow stem, the hollow stem having an outlet opening, the neck having a hole therethrough connecting the inside of the vessel with the inside of the hollow stem, the neck containing a porous plug, said porous plug acting as a filter to retain solids within the vessel when the contents of the vessel are drained through the stem, the stem being looped around the vessel with the outlet opening pointing opposite the top end of the vessel, the stem being looped to prevent the contents of the vessel from exiting the outlet opening until pressure or vacuum is applied to said contents.

2. The reactor vessel of claim 1, wherein the vessel is prepared from high density polyethylene, polyethylene, polypropylene, polytetrafluoroethylene or glass.

3. The reactor vessel of claim 1, wherein the vessel is polypropylene.

4. The reactor vessel of claim 1, wherein the top end of the vessel is capable of being pierced with a cannula for the delivery of material to the vessel.

5. The reactor vessel of claim 1, wherein the porous plug is made of glass, sintered metal, nylon, polysulfone, polycarbonate or polytetrafluoroethylene.

6. The reactor vessel of claim 1, wherein the vessel and the stem are molded as a single unit.

* * * * *